US005965437A

United States Patent [19]
Scadden

[11] Patent Number: 5,965,437
[45] Date of Patent: Oct. 12, 1999

[54] METHOD OF SCREENING A COMPOUND FOR HEMATOPOIETIC ACTIVITY

[75] Inventor: David T. Scadden, Weston, Mass.

[73] Assignee: Beth Israel Deaconess Medical Center, Inc., Boston, Mass.

[21] Appl. No.: 09/107,737

[22] Filed: Jun. 30, 1998

Related U.S. Application Data

[62] Division of application No. 08/299,902, Sep. 1, 1994, Pat. No. 5,827,742.
[51] Int. Cl.$^6$ .............................. G01N 33/48; C12N 5/06
[52] U.S. Cl. .................................. 435/377; 435/2; 435/4; 435/325; 435/375
[58] Field of Search ........................... 435/2, 4, 7.1, 7.21, 435/325

[56] References Cited

U.S. PATENT DOCUMENTS

| | | | |
|---|---|---|---|
| 5,061,620 | 10/1991 | Tsukamoto et al. | 435/7.21 |
| 5,087,570 | 2/1992 | Weissmann . | |
| 5,827,742 | 10/1998 | Scadden . | |

FOREIGN PATENT DOCUMENTS

| | | |
|---|---|---|
| WO 93/25216 | 12/1993 | WIPO . |
| WO 94/11493 | 5/1994 | WIPO . |
| WO 94/16715 | 8/1994 | WIPO . |

OTHER PUBLICATIONS de Haan, G. et al., "Prophylactic Pretreatment of Mice with Hematopoietic Growth Factors Induces Expansion of Primitive Cell Compartments and Results in Protection Against 5–Fluorouracil–Induced Toxicity," Blood, vol. 87, No. 11, 4581–8 (1996).
Hodgson, G.S. et al., "In Vitro Production of CFU–S and Cells with Erythropoiesis Repopulating Ability by 5–Fluorouracil Treated Mouse Bone Marrow," International Journal of Cell Cloning, vol. 1, 49–56 (1983).
Lerner, C. and Harrison, D., "5–Fluorouracil Spares Hemopoietic Stem Cells Responsible for Long–term Repopulation," Exp. Hematol., vol. 18, 114–8 (1990).
Randall, T. and Weissman, I., "Phenotypic and Functional Changes Induced at the Clonal Level in Hematopoietic Stem Cells After 5–Fluorouracil Treatment," Blood, vol. 89, No. 10, 3596–3606 (1997).
Stewart, F. et al., "Post–5–Fluorouracil Human Marrow: Stem Cell Characteristics and Renewal Properties After Autologous Marrow Transplantation," Blood, vol. 81, No. 9, 2283–9 (1993).
Gunji et al. Blood 82: 3283–3289 (1993).
Brandt, J. et al., "Role of c–kit Ligand in the Expansion of Human Hematopoietic Progenitor Cells," Blood, 79(3):634–641 (1992).
Katayama, N. et al., "Growth Factor Requirement for Survival in Cell–Cycle Dormancy of Primitive Murine Lymphohematopoietic Progenitors," Blood, 81(3):610–616 (1993).
Sawada, S. et al., "In Vitro Expansion of Human Peripheral Blood CD34$^+$ Cells," Blood, 82(12):3600–3609 (1993).

Skoda, R.C. et al., "Murine c–mpl: A Member of the Hematopoietic Growth Factor Receptor Superfamily that Transduces a Proliferative Signal," EMBO J., 12(7):2645–2653 (1993).
Takimoto, C.H. et al., "Effects of 5–Fluorouracil Substitution on the RNA Conformation and in Vitro Translation of Thymidylate Synthase Messenger RNA," J. Biol. Chem., 268(28):21438–21442 (1993).
Testa, U. et al., "Cascade Transactivation of Growth Factor Receptors in Early Human Hematopoiesis," Blood, 81(6):1442–1456 (1993).
Youssoufian, H. et al., "Structure, Function, and Activation of the Erythropoietin Receptor," Blood, 81(9):2223–2236 (1993).
Bodine, D.M. et al., "Long–Term In Vivo Expression of a Murine Adenosine Deaminase Gene in Rhesus Monkey Hematopoietic Cells of Multiple Lineages After Retroviral Mediated Gene Transfer Into CD34$^+$ Bone Marrow Cells," Blood, 82(7):1975–1980 (1993).
Smith, C. et al., "Purification and Partial Characterization of a Human Hematopoietic Precursor Population," Blood, 77(10):2122–2128 (1991).
Ogata, H. et al., "Separation of Hematopoietic Stem Cells Into Two Populations and Their Characterization," Blood, 80(1):91–95 (1992).
Briddell, R.A. et al., "Further Phenotypic Characterization and Isolation of Human Hematopoietic Progenitor Cells Using a Monoclonal Antibody to the c–kit Receptor," Blood, 79(12) (1992).
Wineman, J.P. et al., "CD4 is Expressed on Murine Pluripotent Hematopoietic Stem Cells," Blood, 80(7):1717–1724 (1992).
Abboud, M. et al., "Study of Early Hematopoietic Precursors in Human Cord Blood," Exp. Hematol., 20:1043–1047 (1992).
Sprangrude, G.J. and Brooks, D.M., "Phenotypic Analysis of Mouse Hematopoietic Stem Cells Shows a Thy–1–Negative Subset," Blood, 80(8):1957–1964 (1992).
Orlic, D. and Bodine, D.M., "Pluripotent Hematopoietic Stem Cells of Low and High Density Can Repopulate W/W$^v$ Mice," Exp. Hematol., 20:1291–1295 (1992).
Craig, W. et al., "Expression of Thy–1 on Human Hematopoietic Progenitor Cells," J. Exp. Med., 177:1331–1342 (1993).
Srour, E.F. et al., "Long–Term Generation and Expansion of Human Primitive Hematopoietic Progenitor Cells In Vitro," Blood, 81(3):661–669 (1993).

(List continued on next page.)

Primary Examiner—Christina Y. Chan
Assistant Examiner—Phillip Gambel
Attorney, Agent, or Firm—Lahive & Cockfield, LLP

[57] ABSTRACT

Methods of selecting a population of human cells containing quiescent pluripotent hematopoietic progenitor cells substantially free of mature, human myeloid and lymphoid cells, the quiescent pluripotent progenitor cells obtained by these methods, and methods of using the pluripotent progenitor cells are described.

5 Claims, 5 Drawing Sheets

OTHER PUBLICATIONS

Okada, S. et al., "Sequential Analysis of Hematopoietic Reconstitution Achieved by Transplantation of Hematopoietic Stem Cells," *Blood,* 81(7):1720–1725 (1993).

Andrews, R.G. et al., "CD34⁺ Marrow Cells, Devoid of T and B Lymphocytes, Reconstitute Stable Lymphopoiesis and Myelopoiesis in Lethally Irradiated Allogenic Baboons," *Blood,* 80(7):1693–1701 (1992).

Rice, A. et al., "5–Fluorouracil Permits Access to a Primitive Subpopulation of Peripheral Blood Stem Cells," *Stem Cells,* 11:326–335 (1993).

McNiece, I.K. et al., "Detection of a Human CFC With a High Proliferative Potential," *Blood,* 74(2):609–612 (1989).

Li, C.L. and Jonnson, G.R., Long–Term Hemopoietic Repopulation by Thy–1¹°, Lin⁻, Ly6A/E⁺ Cells, *Exp. Hematol.,* 20:1309–1315 (1992).

Gabbianelli, M. et al., "'Pure' Human Hematopoietic Progenitors: Permissive Action of Basic Fibroblast Growth Factor," *Science,* 249:1561–1564 (1990).

Ploemacher R.E. and Brons, N.H.C., "In Vivo Proliferative and Differential Properties of Murine Bone Marrow Cells Separated on the Basis of Rhodamine–123 Retention," *Ex. Hematol,* 16:903–907 (1988).

Sprangrude, G.J. et al., "Purification and Characterization of Mouse Hematopoietic Stem Cells," *Science,* 241:58–62 (1988).

Jones, R.J. et al., "Separation of Pluripotent Hematopoietic Stem Cells from Spleen Colony–Forming Cells," *Nature,* 347:188–189 (1990).

Cassel, A. et al., "Retroviral–Mediated Gene Transfer into CD34–Enriched Human Peripheral Blood Stem Cells," *Exp. Hematology,* 21:585–591 (1993).

Brenner, M.K. et al., "Gene Marking to Determine Whether Autologous Marrow Infusion Restores Long–Term Haemopoiesis in Cancer Patients," *The Lancet,* 342:1134–1137 (1993).

Van Beusechem, V.W. et al., "Retrovirus–Mediated Gene Transfer into Rhesus Monkey Hematopoietic Stem Cells: The Effect of Viral Titers on Transduction Efficiency," *Human Gene Therapy,* 4:239–247 (1993).

Brandt, J. et al., "Characterization of a Human Hematopoietic Progenitor Cell Capable of Forming Blast Cell Containing Colonies In Vitro," *J. Clin. Invest.* 82:1017–1027 (1988).

Ophir, A. et al., "5–Fluorouracil and Mast Cell Precursors in Mice," *Exp. Hematology,* 21:1558–1562 (1993).

Gordon, M.Y, "Human Haemopoietic Stem Cell Assays," *Blood Reviews* 7:190–197 (1993).

Berardi, A.C. et al., "Isolation and Characterization of Human Bone Marrow Hematopoietic Progenitor Cells in $G_0$ Phase," *Workshop on Hematopoietic Stem Cell Purification and Biology,* p. 12a (1993) Abstract No. 38.

Reisbach, G. et al., "Characterization of Hemopoietic Cell Populations From Human Cord Blood Expressing c–kit" *Exp. Hematology,* 21:74–79 (1993).

Harrison, D.E. and Lernear, C.P., "Most Primitive Hematopoietic Stem Cells are Stimulated to Cycle Rapidly After Treatment with 5–Fluorouracil," *Blood,* 78(5):1237–1240 (1991).

Bodine, D.M. et al., "In Vivo Administration of Stem Cell Factor to Mice Increased the Absolute Number of Pluripotent Hematopoietic Stem Cells," *Blood,* 82(2):445–455 (1993).

Koller, M.R. et al., "Large–Scale Expansion of Human Stem and Progenitor Cells From Bone Marrow Mononuclear Cells in Continuous Perfusion Cultures," *Blood,* 82(2):378–384 (1993).

Bradley, T.R. et al., "Multiple Growth Factor Requirements of Mouse Bone Marrow Cells," *Exp. Hematology,* 16(6) (1988) Abstract No. 14.

NcNeice, I.K. et al., "Human Bone Marrow Progenitor Cell Populations," *Exp. Hematology,* 16(6) (1988) Abstract No. 359.

Iscove, N.N. et al., "A Soluble Activity From Adherent Marrow Cells Cooperates With IL 3 in Stimulating Growth of Pluripotential Hematopoietic Precursors," *Blood,* 71(4):953–957 (1988).

Suda, T. et al., "Permissive Role of Interleukin 3 (IL–3) in Proliferation and Differentiation of Multipotential Hemopoietic Progenitors in Culture," *J. Cell. Physiol.,* 124:182–190 (1985).

Stewart, F.M. et al., "Post–5–Fluorouracil Human Marrow: Stem Cell Characteristics and Renewal Properties After Autologous Marrow Transplantation," *Blood,* 81(9):2283–2289 (1993).

Civin, C.I. et al., "Antigenic Analysis of Hematopoiesis. III. A Hematopoietic Progenitor Cell Surface Antigen Defined by a Monoclonal Antibody Raised Against KG–1a Cells," *J. Immunol.,* 135(1):157–165 (1984).

Sutherland, H.J. et al., "Functional Characterization of Individual Human Hematopoietic Stem Cells Cultured at Limiting Dilution on Supportive Marrow Stromal Layers," *Proc. Natl. Acad. Sci. USA,* 87:3584–3588 (1990).

Spangrude, G.J. and Johnson, G.R., "Resting and Activated Subsets of Mouse Multipotent Hematopoietic Stem Cells," *Proc. Natl. Acad. Sci. USA,* 87:7433–7437 (1990).

Ploemacher, R.E. et al., "An In Vitro Limiting–Dilution Assay of Long–Term Repopulating Hematopoietic Stem Cells in the Mouse," *Blood,* 74(8):2755–2763 (1989).

Yamasaki, K. et al., "Cloning and Expression of the Human Interleukin–6 (BSF–2/IFNβ 2) Receptor," *Science,* 241:825–828 (1988).

Hibi, M. et al., "Molecular Cloning and Expression of an IL–6 Signal Transducer, gp130," *Cell.,* 63:1149–1157 (1990).

Gearing, D.P. et al., "The IL–6 Signal Transducer, gp130: An Onconstatin M Receptor and Affinity Converter for the LIF Receptor," *Science,* 255:1434–1437 (1992).

Escary, J–L. et al., "Leukaemia Inhibitory Factor is Necessary for Maintenance of Hematopoietic Stem Cells and Thymocyte Stimulation," *Nature,* 363:361–364 (1993).

Dexter, M. and Allan T., "Multi–Talented Stem Cells?" *Nature,* 360:709–719 (1992).

Huang, S. and Terstappen, L.W.M.M., "Formation of Hematopoietic Microenvironment and Hematopoietic Stem Cells From a Single Human Bone Marrow Stem Cells," *Nature,* 360:745–749 (1992).

Brandt, J. et al., "Detection of a Human Hematopoietic Progenitor Cell Capable of Forming Blast Cell Containing Colonies In Vitro," *Adv. Exp. Med. Biol.,* 241:165–173 (1988).

Reisner, Y. et al., "Enrichment for CFU–C from Murine and Human Bone Marrow Using Soybean Agglutinin," *Blood,* 95(2):360–363 (1992).

Civin, C.I. et al., "Antigenic Analysis of Hematopoiesis. VI. Flow Cytometric Characterization of My–10–positive Progenitor Cells in Normal Human Bone Marrow," *Exp. Hematol.,* 15:10–17 (1987).

Kriegler A.B et al., The Relatinoship Between Different High Proliferative Potential Colony–Forming Cells in Mouse Bone Marrow, *Exp. Hematology,* 22:423–440 (1994).

Lerner, C. and Harrison, D.E., "5–Fluorouracil Spares Hemopoietic Stem Cells Responsible for Long–Term Repopulation," *Exp. Hematol.,* 18:114–118 (1990).

Wolf, N.S., et al., "In Vivo and In Vitro Characterization of Long–Term Repopulating Primitive Hematopoietic Cells Isolated by Sequential Hoechst 33342–Rhodamine 123 FACS Selection," *Exp. Hematol.,* 21:614–622 (1993).

Yamaguchi, Y. et al., "Expression of c–kit mRNA and Protein During the Differentiation of Human Hematopoietic Progenitor Cells," *Exp. Hematol.,* 21:1233–1238 (1993).

Ebell, W. et al., "Depletion of Stromal Cell Elements in Human Marrow Grafts Separated by Soybean Agglutinin," *Blood,* 65(5):1105–1111 (1985).

Terstappen, L.W.M.M. et al., "Sequential Generations of Hematopoietic Colonies Derived From Single Nonlineage––Committed $CD34^+CD38^-$ Progenitor Cells," *Blood,* 77(6):1218–1227 (1991).

Zipori, D. and Lee, F., "Introduction of Interleukin–3 Gene Into Stomal Cells From the Bone Marrow Alters Hemopoietic Differentiation but Does not Modify Stem Cell Renewal," *Blood,* 71(3):586–596 (1988).

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: synthetic DNA (xi) SEQUENCE DESCRIPTION: SEQ ID NO:1:

ATGTCGTCCA GGCCGCTCTG GACAAAATAT GAATTC                                   36

(2) INFORMATION FOR SEQ ID NO:2:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ii) MOLECULE TYPE: synthetic DNA (xi) SEQUENCE DESCRIPTION: SEQ ID NO:2:

CAGATCAGCT GGGAGGAGCC AAGCACTGAA CTTCACCGTC GC                            42

(2) INFORMATION FOR SEQ ID NO:3:

(i) SEQUENCE CHARACTERISTICS:
         (A) LENGTH: 52 base pairs
         (B) TYPE: nucleic acid
         (C) STRANDEDNESS: single
         (D) TOPOLOGY: linear (ii) MOLECULE TYPE: synthetic DNA (xi) SEQUENCE DESCRIPTION: SEQ ID NO:3:

ATAGCAGCCC AGGGCACTTC AGAGTAAGAG GGCTTGGGAA GATCTTTTAA AA                 52

(2) INFORMATION FOR SEQ ID NO:4:

(i) SEQUENCE CHARACTERISTICS:
         (A) LENGTH: 50 base pairs
         (B) TYPE: nucleic acid
         (C) STRANDEDNESS: single
         (D) TOPOLOGY: linear (ii) MOLECULE TYPE: synthetic DNA (xi) SEQUENCE DESCRIPTION: SEQ ID NO:4:

CTTACTTAGG TGTGGGGGAA GCACCATAAC TTGTTTAGCC CAAAACCAAG                    50

(2) INFORMATION FOR SEQ ID NO:5:

(i) SEQUENCE CHARACTERISTICS:
         (A) LENGTH: 45 base pairs
         (B) TYPE: nucleic acid
         (C) STRANDEDNESS: single
         (D) TOPOLOGY: linear -continued (ii) MOLECULE TYPE: synthetic DNA (xi) SEQUENCE DESCRIPTION: SEQ ID NO:5:

CTGTACGGCA AGGCGGCTAC ATGCCTCAGT GAAGGACTAG TAGTT                45

METHOD OF SCREENING A COMPOUND FOR HEMATOPOIETIC ACTIVITY

This application is a divisional application of Ser. No. 08/299,902 filed on Sep. 1, 1994, now U.S. Pat. No. 5,827,742. The contents of all of the aforementioned application(s) are hereby incorporated by reference.

GOVERNMENT FUNDING

This invention was made in whole, or in part, with support from the National Institutes of Health. The United States Government has certain rights in the invention.

BACKGROUND OF THE INVNENTION

Hematopoietic stem cells are a population of cells capable of both self renewal and of differentiation into a variety of hematopoietic lineages. (S. Huang and L. Terstappen, Nature, 360:745–749 (1992)). The definition of the hematopoietic stem cell is functional and based upon the ability of transplanted cells to repopulate the hematopoietic system of a recipient who has undergone myeloablative treatment. The prevailing view is that stem cells represent perhaps 0.01 percent of bone marrow cells, that they can self-renew and that they can be assayed by their ability to regenerate the bone marrow and to give rise to long-term lympho- and myelopoiesis. (M. Dexter and T. Allen, Nature, 360:709–710 (1992)).

The differentiation of hematopoietic cells from primitive multipotent progenitors to mature blood elements involves a series of lineage commitment steps accompanied by the acquisition of specific phenotypic characteristics. Cells gain or lose antigenic features and responsiveness to specific cytokines based on their lineage and stage of differentiation.

The efficient isolation of hematopoietic stem cells would enhance both the investigation of the processes of lineage commitment and self-renewal and the clinical strategies of bone marrow transplantation and hematopoietic cell gene therapy. However, identification of such primitive cells is challenging because of their apparent low frequency and their lack of identifiable morphologic features.

Several methods of enrichment have been developed based on immunologic and certain functional properties of primitive hematopoietic cells. For example, antibodies have been generated which recognize cell surface antigens associated with hematopoietic cells at various stages of lineage differentiation. Immunophenotypes which are enriched for fractions of human bone marrow cells with more primitive phenotypes are CD34+, CD33−, CD38−, HLA DR−, Thy-1$^{lo}$ and negative staining for lineage specific antigens (W. Craig, et al., J. Exp. Med. 177:1331 (1993); C. I. Civin et al., J. Immunol. 133:157 (1994); C. I. Civin, et al., Exp. Hematol. 15:10 (1987); L. W. M. M. Terstappen, et al., Blood 77:1218 (1991)). In addition, it has been recognized that low intensity of staining with the dye, Rhodamine$_{123}$ (Rho), is associated with a fraction of bone marrow cells enriched for repopulating stem cells (R. E. Ploemacher, N. H. C. Brons, Exp. Hematol. 16:903 (1988); N. S. Wolf, et al., Exp. Hematol. 21:614 (1993); G. J. Spangrude, G. R. Johnson, Proc. Natl. Acad. Sci. U.S.A. 87:7433 (1990)).

These methods, however, depend upon technically demanding cell sorting which involves considerable mechanical manipulation of the cells. Further, antibody binding to cell surface structures may theoretically be capable of inducing perturbations of the cells' physiology.

Enrichment methods have been developed which exploit the observations that soy-bean agglutinin binding is uncommon in primitive bone marrow cells (Y. Reisner, et al., Blood 59:360 (1992); W. Ebell, et al., Blood 65:1105 (1985)) and that stem cells are relatively resistant to the toxic effects of the alkylating agent, 4-hydroxycyclophosphamide (4-HC) (M. Y. Gordon, et al., Leukemia Res. 9:1017 (1985); C. Smith, et al., Blood 77:2122 (1991)). The anti-metabolite, 5-fluorouracil (5-FU), when added to short-term bone marrow cultures was noted to enrich for early hematopoietic cells, presumably due to the relative quiescence of more primitive cells (C. Lemer, D. Harrison, Exp. Hematol. 18:114 (1990); M. F. Stewart et al., Blood 81, 2283 (1993)). However, these methods also suffer from limited selectivity, yielding relatively heterogeneous populations of precursor cells. Thus, a need still exists for an efficient method of isolating hematopoietic stem cells.

SUMMARY OF THE INVENTION

The present invention relates to methods of selecting a population of human cells containing quiescent pluripotent hematopoietic progenitor cells. The population of cells selected by the methods described herein are substantially free of mature myeloid and lymphoid cells. That is, the methods described herein select a substantially pure population of human stem cells. The methods described herein are based on the observation that hematopoietic cells differentiate in response to growth factors, and that proliferating cells are sensitive to anti-metabolite treatment. Since hematopoietic cells acquire responsiveness to specific growth factors in a hierarchial fashion as they undergo differentiation, the combination of growth factor stimulation with anti-metabolite treatment induces cell death in the growth factors responsive cells, thus selecting for immature hematopoietic cells resistant to the proliferative effects of the growth factors.

The quiescent pluripotent hematopoietic progenitor cells are isolated from a mammalian hematopoietic cell suspension. In particular, mononuclear cells are obtained from human bone marrow, but may also be obtained from peripheral blood, umbilical cord blood or fetal liver cells. In one embodiment of the present invention, the mononuclear cell suspension is contacted with an antibody specific for a cell surface antigen expressed by immature hematopoietic precursor cells, such as colony-forming units. Examples of such a cell-surface antigen include c-kit, CD34 and Thy-1. The antibody will bind only to the immature hematopoietic precursor cells, which can be separated from the more mature precursor cells by routine methods used to recover antibody bound cells.

In the present invention, the mononuclear cell suspension, or the suspension of antibody-treated mononuclear cells, is then cultured in the presence of at least one anti-metabolite and at least one early-acting growth factor. As used herein, an anti-metabolite is defined as any agent capable of inhibiting the normal metabolic process of a dividing cell. Normal metabolic process can include, for example, DNA synthesis, RNA splicing, protein synthesis, or nutrient transport or metabolism. As used herein, an early-acting growth factor can include any growth factor, or cytokine, which induces the proliferation of earliest identifiably committed progenitor cells. For example, the cytokine IL-3 is active on multipotential progenitor cells and has been demonstrated to have an effect on the early differentiation of many hematopoietic cells, pre B-cells, and granulocyte-macrophage colony-forming cells and high proliferative potential colony forming cells (HPP-CFC1) (Kriegler et al., Exp.

*Hematology,* 22:432 (1994)). This response is augmented by the presence of kit ligand. (Suda, T. et al., *J. Cell. Physiol.,* 124:182–190 (1985)). The suicide-selection technique described herein excludes cells that are proliferating in response to the early-acting growth factors. Thus, using the method described herein, a population of cells is selected which is significantly enriched for quiescent, primitive hematopoietic progenitor cells, and substantially free of mature lymphoid and myeloid cells. The degree of enrichment is greater than that typically achieved by antigen selection or flow cytometic methods of stem cell isolation and avoids problems associated with those methods.

This invention further relates to isolated quiescent, pluripotent hematopoietic progenitor cells, substantially free of mature human myeloid and lymphoid cells, obtained by the methods described herein. These cells are characterized as being quiescent (in $G_o$-phase), long term culture-initiating cells (LTC-IC) with a CD34+, CD38–, CD33–, HLA-DR–, CD45Ra–, CD19– and C-kit+ immunophenotype. Single cell cultures of the quiescent, pluripotent progenitor cells are capable of yielding both myeloid and lymphoid progeny. Analysis of individual cells indicated that this primitive subset of cells expressed characteristics of hematopoietic stem cells which have not been previously shown in isolated populations of primitive cells. These characteristics included mRNA for c-kit, gp130, c-mpl and the interleukin-1 and interleukin-6 receptors, but not for the alpha subunit of the GM-CSF receptor. Thus, the cell population selected by the method described herein is capable of restoring the production of hematopoietic and lymphoid cells, that is, repopulating the hematopoietic system.

Also encompassed by the present invention are methods of using the quiescent, primitive hematopoietic progenitor cells. Cells selected by the method described herein can be used in a screening assay to screen naturally occurring, or synthetically produced compounds for hematopoietic activity (e.g., compounds that induce hematopoiesis). For example, using the quiescent, pluripotent progenitor cells described herein, it is possible to characterize the cytokine stimuli and adhesive interactions which will trigger the quiescent stem cell population into cell cycle or to differentiate.

The cells isolated by the present method have the above-described characteristics which are consistent with repopulating stem cells. Thus, these cells are useful for stem cell transplantation and can be used in place of conventionally obtained bone marrow in clinical situations requiring bone marrow transplants, such as in the treatment of various leukemias.

The quiescent stem cells obtained by this method can be used in methods of stem cell gene transduction to introduce foreign genes into hematopoietic progenitor and stem cells, thus, avoiding problems of immunologic reactivity, such as graft rejection or graft-versus-host disease, may permit isolation of normal stem cells away from contaminating malignant cells or virally infected cells and may permit small volume storage of donor material.

DETAILED DESCRIPTION OF THE INVENTION

Figure 1:
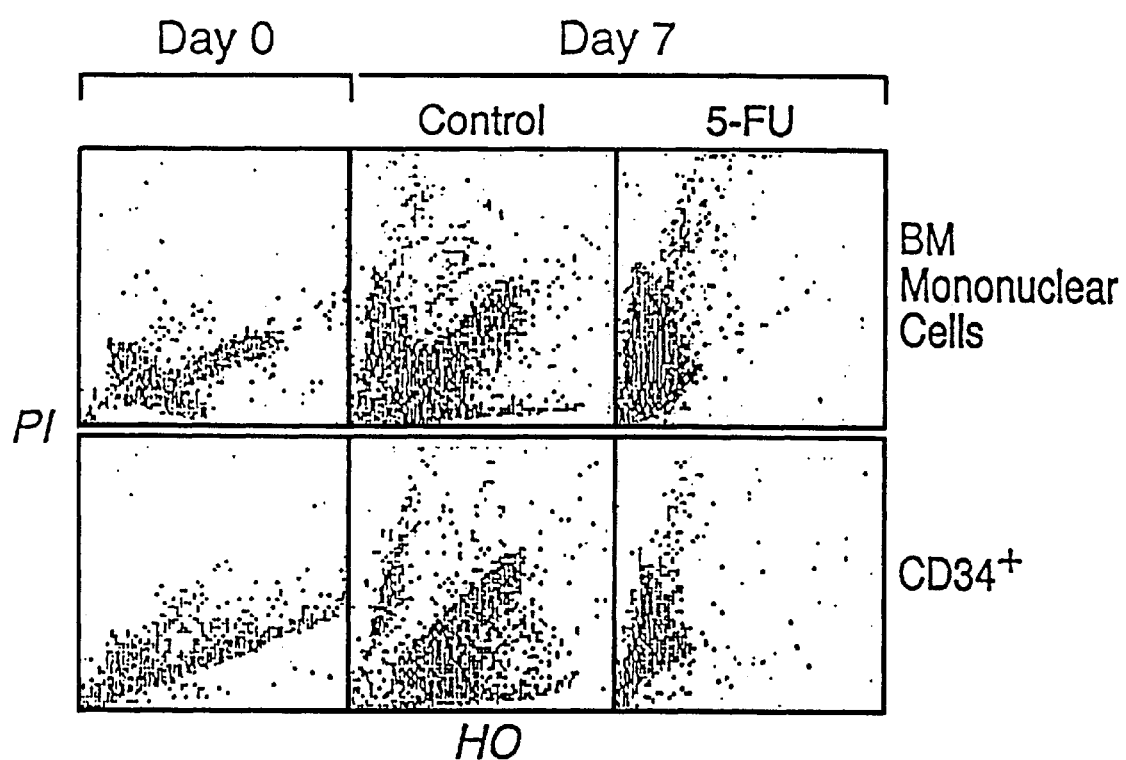
FIG. 1 depicts the results of an experiment showing cell cycle status of CD34+ (lower panel) or unselected (upper panel) bone marrow monoclear cells cultured under control or 5-FU selected conditions.

The present invention relates to methods of selecting a population of human cells containing quiescent pluripotent hematopoietic progenitor cells. This population of cells is substantially free of mature myeloid and lymphoid cells. The methods described herein are based, in part, on the observation that hematopoietic stem cells differentiate in response to cytokines and growth factors. The methods described herein are also based, in part, on the observation that proliferating cells are sensitive to anti-metabolite treatment. Thus, the strategy of the present invention is one of suicide selection, wherein hematopoietic precursor cells responsive to early-acting cytokines are forced to growth stimulation and, consequently, metabolic death, resulting in the highly specific selection of quiescent, pluripotent hematopoietic progenitor cells.

This population of cells can be selected from any source of hematopoietic cells, including adult and fetal mammalian tissues such as spleen, liver, thymus and bone marrow, as well as peripheral blood. These cells are obtained using routine laboratory methods. As described in Example 1, quiescent pluripotent hematopoietic progenitor cells are selected from a human's bone marrow source. A cell suspension is prepared as described in Example 1, to isolate low-density mononuclear cells from the hematopoietic cell source.

The mononuclear hematopoietic cells were cultured, also as described in Example 1, in the presence of at least one anti-metabolite and early-acting growth factor. Since hematopoietic cells acquire responsiveness to specific cytokines in an hierarchical fashion as they undergo differentiation, combining cytokine stimulation with anti-metabolite treatment induces cell death in responding cells, selecting for cells resistant to the proliferative effects of the cytokines. This method allows for the selective depletion of subsets of differentiated cells.

Early-acting cytokines which induce the proliferation of the earliest identifiably committed progenitor cells are suitable for use in the present invention. Specifically, the combination of kit ligand (KL) (or also referred to herein as kit ligand stem cell factor, or SCF) and interleukin-3 (IL-3) has been identified to stimulate primitive cells capable of forming high proliferative capacity colonies type 1 (HPP-CFC-1), an in vitro marker of a very primitive myeloid cell (A. B. Krigler, et al., *Exp. Hem.* 22:432 (1994); J. E. Brandt, et al.,

*Blood* 79:634. (1992); R. A. Briddell et al., *Blood* 7:3159 (1992); Y. Yamaguchi et al., *Exp. Hematol.* 21:1233 (1993); H. Ogata et al., *Blood* 80:91 (1992)). However, the IL-3 receptor has not been observed on the hematopoietic stem cell (D. Zipori, F. Lee, *Blood* 71:586 25 (1988)). Based on these observations of cellular responsiveness, the combination of these cytokines was predicted to induce a response in all cells with identifiable myeloid differentiation features, sparing true stem cells. Other early acting cytokines and growth factors suitable for use in the present invention include IL-1, IL-6, IL-11, flt-3 ligand and mpl ligand. A single suitable early-acting growth factor can be used in the present invention, or a combination of more than one factor can be used. Concentrations of growth factors used will vary according to the factor, or combination of factors used. Effective amounts of growth factors are known to those of skill in the art. However, an effective amount of growth factor as defined herein, is an amount of growth factor which stimulates the proliferation or differentiation of a hematopoietic precursor cell in a phenotypically detectable manner. For example, the differentiated hematopoietic cell can be identified based on immunologic properties, such as the expression of a cell surface antigen.

A single suitable anti-metabolite can be used in the present invention, or a combination of more than one anti-metabolites can be used. Suitable anti-metabolites include 5-fluorouracil (5-FU), bromodeoxyuridine (BudR) methotrexate and $^3$H-thymidine other suitable anti-metabolite agents are known to those of skill in the art. As described in Example 1, 5-fluorouracil was used.

Concentrations of anti-metabolites used will vary according to the anti-metabolite. Effective amounts of anti-metabolites are known to those of skill in the art. However, an effective amount of anti-metabolite, as defined herein, is an amount of anti-metabolite capable of causing metabolite death in proliferating cells. Cell death can be determined using known laboratory methods, such as dye uptake. As described in Example 1, high concentrations (e.g., greater than 200 mcg/ml) of 5-FU were effective to cause metabolic death of proliferating mononuclear hematopoietic cells. Mononuclear hematopoietic cells were cultured in the presence of at least one early acting growth factor and at least one anti-metabolite under conditions sufficient to eliminate proliferating (i.e., actively dividing) cells. Typically, the culture time period lasted several days. As described in Example 1, the cells were cultured for approximately seven days, although the cells can be maintained in culture for a period based on the specific cell type to be isolated. A period as long as 10 days did not effect the outcome of these experiments. By performing the selection method over a period of several days, mature mononuclear cells are selected against via a metabolically-induced cell death and virtually all cellular elements downstream of differentiation points where cytokine responsiveness is acquired are eliminated.

As described in Example 1, the ability to select for cells which were not actively cycling following growth factor treatment was assessed by flow cytometric analysis using DNA staining dyes. FIG. 1 indicates that when using either unfractionated bone marrow mononuclear preparations or CD34+ bone marrow cells, the selection strategy efficiently eliminated cells in S or $G_2$ phase. The events that occur from one cell division to the next are termed the cell cycle. The total time for a complete cell cycle varies considerably (from minutes to days) for different cell types and under different growth conditions. Following cell division, each daughter cell enters a period of accelerating biosynthetic activity called the $G_1$ phase. $G_1$ ends with duplication of chromosomal DNA. This period of genome replication is called the synthesis-phase or S-phase. The completion of the S-phase leads to mitosis and cytokinesis (cell separation) during the M-phase. Under certain conditions are arrested in $G_1$ not undergoing cell division and are said to be in a $G_0$-phase.

Testing a number of different selection strategies, it was determined that the maximal efficiency was attained when high concentrations of 5-FU were used (>200 mcg/ml) and when selection was performed for a minimum of 7 days. At high concentrations, 5-FU is capable of inhibiting RNA splicing as well as DNA synthesis and may therefore act to more effectively eliminate metabolically activated cells (C. H. Takimoto et al., *J. Biol. Chem.* 268:21438 (1993); M. Inaba, et al., *Jpn. J. Cancer. Res.* 81:1039 (1990)). The prolonged incubation of the mononuclear cells with specific growth factors, low serum concentration and anti-metabolites result in culture conditions which fail to support the viability of mature lymphoid or myeloid cells.

In another embodiment of the present invention, the mononuclear hematopoietic cell preparation is contacted with an antibody specific for a cell surface antigen expressed by immature hematopoietic precursor cells prior to culture with growth factors and anti-metabolites. This step acts as a pre-selection step to fractionate immature hematopoietic cells, (i.e., cells that although not fully differentiated, are already committed to a particular cell lineage) from more primitive hematopoietic cells. Such an antibody can be a polyclonal, or a monoclonal antibody, and include, for example, anti-CD34, anti-thy-1 or anti-kit. As described in Example 1, non-adherent, mononuclear cells were incubated with anti-CD34 antibody under conditions sufficient for the antibody to bind to cells expressing the CD34 antigen. The CD34+ cells were separated from CD34− cells using routine laboratory methods and then cultured with anti-metabolite and growth factors as described above for unfractionated cells. After culturing, cells were recovered by standard laboratory techniques to obtain a population of cells significantly enriched for quiescent, pluripotent hematopoietic progenitor cells.

Figure 2:
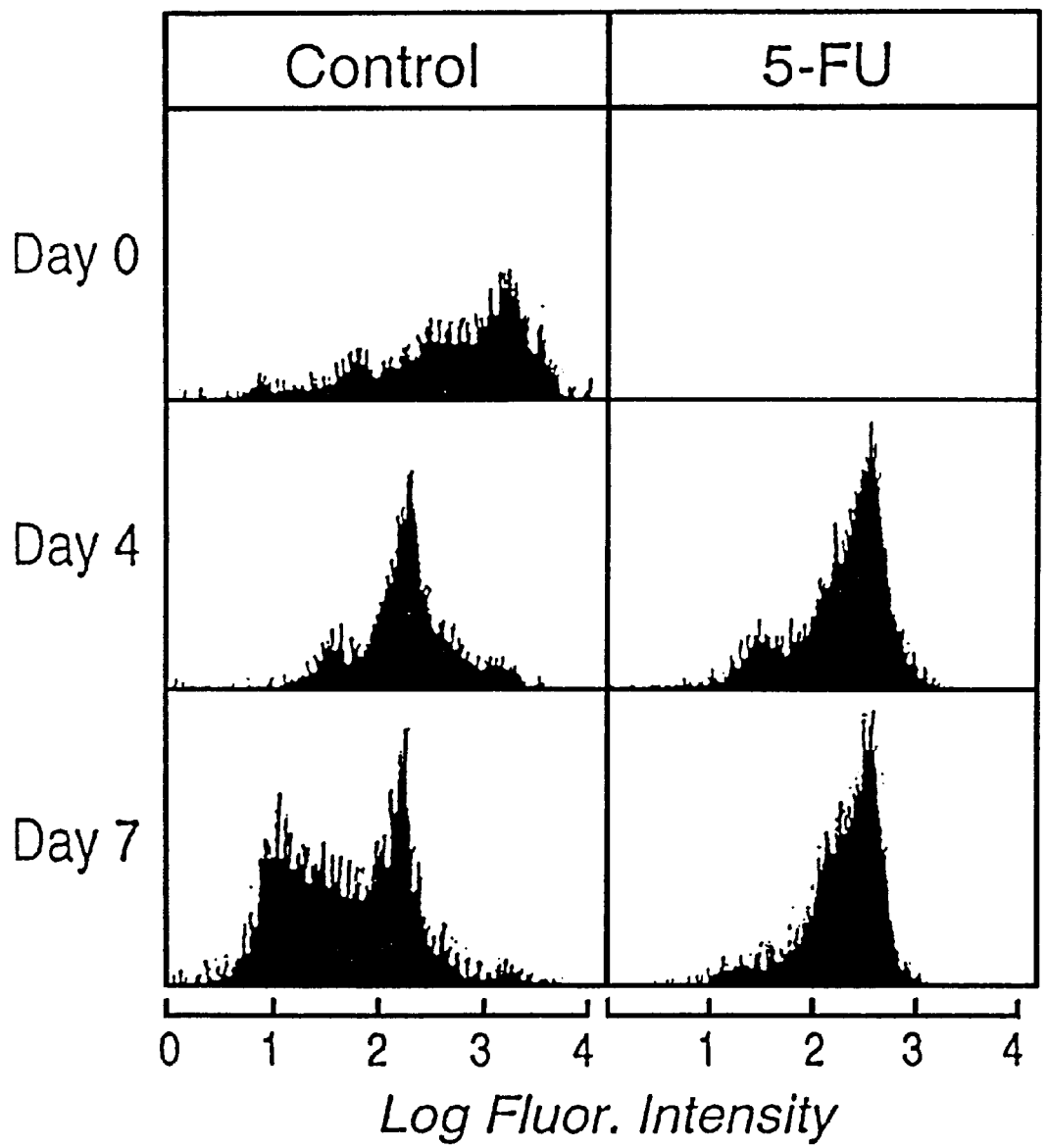
FIG. 2 depicts the results of an experiment showing that cytokine plus 5-FU treatment selects for cells that have not undergone cell division.

The isolated hematopoietic progenitor cells were evaluated for their resistance to the proliferative effects of kit ligand stem cell factor (KL) and IL-3 by using the membrane dye PKH26 as described in Example 2. This fluorescent dye is stable in cell membranes with variable staining based on the cell type. As cells divide, the dye partitions in daughter cells yielding an exponential decrease in the per cell fluorescence intensity. FIG. 2 demonstrates that during the selection process, $PKH26_{bright}$ were enriched and unlike control cells, did not decline in peak fluorescence intensity, demonstrating the selective isolation of a non-dividing subset of bone marrow mononuclear cells.

As described in Example 3, the morphology of bone marrow mononuclear cells cultured in the presence of IL-3 and KL with or without 5-FU for seven days was assessed. Morphologically the residual cells were small in size (6 microns) with dense chromatin and a faint halo of cytoplasm (FIG. 3). Immunophenotypic analysis was performed by fluorescence microscopy on cytocentrifuged preparations by two independent readers who scored remarkably uniform characteristics for all available cells. No cells stained with markers for potentially contaminating quiescent lymphoid cells, CD19 or CD45Ra, or for more differentiated progenitor cells, CD38, CD33, HLA-DR. In contrast, all cells scored positively for CD34 and c-kit. These latter markers have been reported to be present on cells capable of providing multi-lineage human hematopoietic tissue in a chimeric fetal sheep model (E. F. Srour et al., *Blood* 82:333 (1993)). The particular combination of markers present on the selected cells matches that found by a number of other investigators to identify a subset of very primitive hematopoietic cells (W. Craig, et al., *J. Exp. Med.* 177:1331 (1993); C. I. Civin et al., *J. Immunol.* 133:157 (1994); C. I. Civin, et al., *Exp. Hematol.* 15:10 (1987); L. W. M. M. Terstappen, et al., *Blood* 77:1218 (1991)). The yield of cells selected by the present method was approximately 1 in every $10^5$ bone marrow mononuclear cells.

Functional characterization of human hematopoietic progenitor cells depends upon in vitro assays. Although immunodeficient animal models are being developed to assess the in vivo repopulating ability of human cells, the number of cells required for these assays is generally prohibitive for evaluating subsets of CD34+ marrow cells. Thus, a number of in vitro assays have been developed to evaluate repopulating ability. The assay which has been most rigorously shown to correlate with repopulating ability in the mouse has been adapted to human cells and is termed the long-term culture-initiating cell assay (LTC-IC). (R. E. Ploemacher, et al., *Blood* 74:2755 (1989); I. K. McNiece, et al., *J. of Cell Cloning* 8:146 (1990)).

As described in Example 4, functionally selected bone marrow mononuclear cells ($G_o$ cells) are capable of generating colonies of mixed lineage only upon prolonged co-cultivation with bone marrow stroma feeder layers. Cells selected in KL, IL-3 and 5-FU were uniformly incapable of forming colonies in methylcellulose upon completion of the selection process despite supplementation with multiple combinations of early and late acting cytokines. However, Cfu-mix colonies were noted after approximately three weeks of co-cultivation with bone marrow stroma.

To quantitatively assess the ability of the selected cells to generate more differentiated cells over time, a 96-well plate LTC-IC assay was used, as described in Example 5. (H. J. Sutherland, et al., *Proc. Natl. Acad. Sci. U.S.A.* 87:3584 (1990)). Cells were plated using the Becton-Dickenson cell dispersion unit which has an accuracy of plating of 0.1% (S. Huang, L. W. M. M, Terstappen, *Blood* 83:1515 (1994)) to provide 24 wells each of 0, 1, 5, 10 or 100 cells/well, as described in Example 5. The fraction of 1 cell/well samples yielding colonies after 5 weeks of co-cultivation with stroma followed by 2 weeks in methylcellulose in 5 independent experiments was 73% (95% C.I. +/−8%) (Table 1).

TABLE 1

| | SINGLE CELL LTC-IC | | | |
|---|---|---|---|---|
| EXPERIMENT | +/TOTAL | % | +/TOTAL | % |
| 1 | 17/19 | 89 | 17/24 | 71 |
| 2 | 19/21 | 90 | 19/24 | 79 |
| 3 | 19/21 | 90 | 19/24 | 79 |
| 4 | 17/78 | 94 | 17/24 | 71 |
| 5 | 15/18 | 83 | 15/24 | 63 |
| MEAN | | 89 | | 73 |
| 95% C.I. | | 5 | | 8 |

When normalized for the maximal number of wells scoring positive in the 5, 10 or 100 cells/well samples, thought to reflect the supportive capacity of the irradiated feeder layer, the percent positive was 89% (95% C.I. +/−5%). This compares favorably with the highest yield reported with any other subselection technique for bone marrow cells (H. J. Sutherland, et al., *Proc. Natl. Acad. Sci. U.S.A.* 87:3584 (1990)) and was significantly better than CD34+ bone marrow cells compared in our assay (p<0.001) (H. J. Sutherland, et al., *Proc. Natl. Acad. Sci. U.S.A.* 87:3584 (1990)).

Figure 3A:
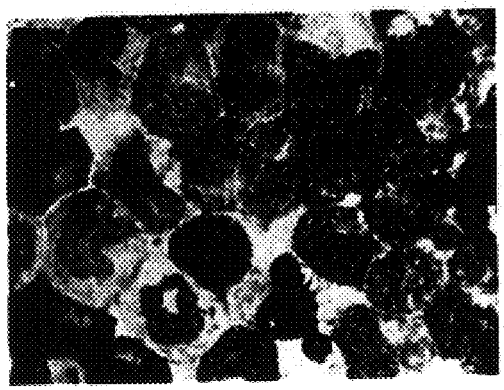
FIG. 3A–3E is a series of photo-micrographs illustrating the morphology of CD34+ bone marrow monoclear cells cultured in the presence of IL-3 and KL with (A) or without (B) 5-FU for seven days. Following single cell long term bone marrow culture, progeny were variable in size with some clusters of large cells (C) (magnification 400×) staining positively for monocyte specific alpha-naphthyl esterase (D); dispersed cells and some clustered larger cells were negative for alpha-naphthyl esterase. Smaller, dispersed cells (magnification 1000×) stained positively for the B-cell specific CD19 (D); clustered, large cells were negative for CD19.
Figure 3C:
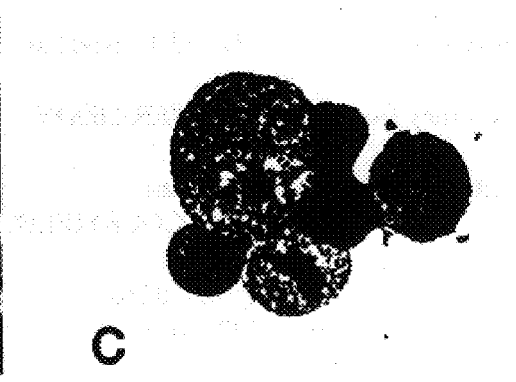
Figure 3B:
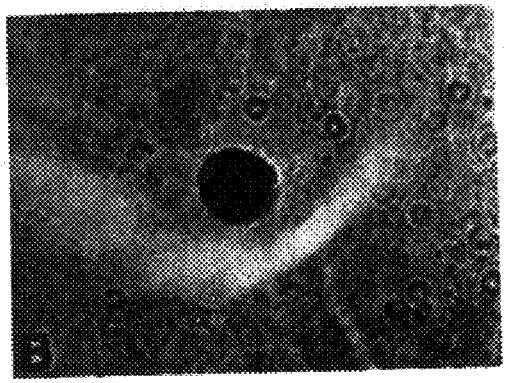
Figure 3D:
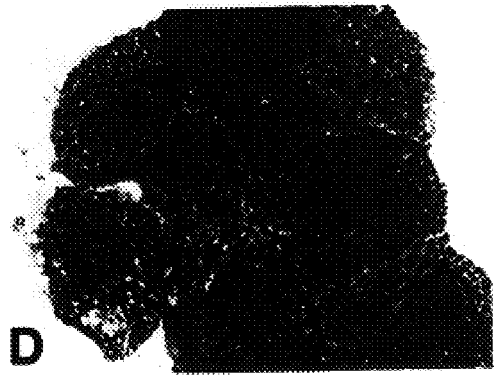
Figure 3E:
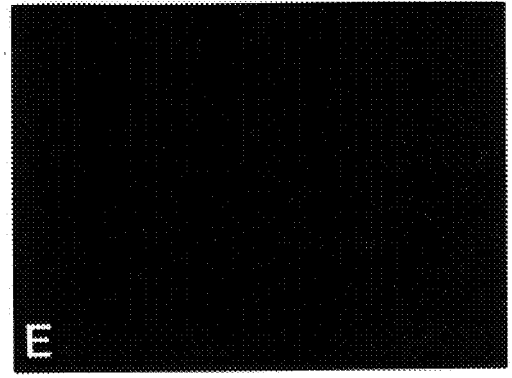

The differentiative capacity of the selected cells was also evaluated. Specifically whether the selected cells were capable of differentiating along lymphoid as well as myeloid lineages was tested. First, it was confirmed that under the standard Dexter culture conditions (T. M. Dexter, et al., *J. Cell Physiol.* 91:335 (1976)), individually plated selected cells produced progeny that histochemically stained positively for the monocytic enzyme alpha-naphthyl esterase. The selected cells were thereby considered capable of maturing along myeloid lines, specifically producing monocytoid cells in liquid culture. Single cell preparations were then cultivated under Dexter culture conditions for 4 weeks and then switched to culture conditions adapted from the lymphoid supporting Whitlock-Witte cultivation system. This modification has been previously demonstrated in murine systems to result in the production of both myeloid and lymphoid cell elements (C. A. Whitlock and O. N. Witte, *Proc. Natl. Acad. Sci. U.S.A.* 79:3608 (1982); C. A. Whitlock, et al., *Immunol. Method* 67:353 (1984); M. E. Lemieux, et al., *Blood* 82:13a (1993)). Cells derived from these culture conditions were aliquoted and stained for B-cell specific markers (CD 19) as well as esterase staining. FIG. 3A and 3D demonstrates that single cells were capable of yielding both myeloid (esterase +) and lymphoid (CD19+) progeny. These data are consistent with the conclusion that the selected subpopulation of bone marrow cells had multi-lineage potential in addition to having LTC-IC functional capacity.

Figure 4A:
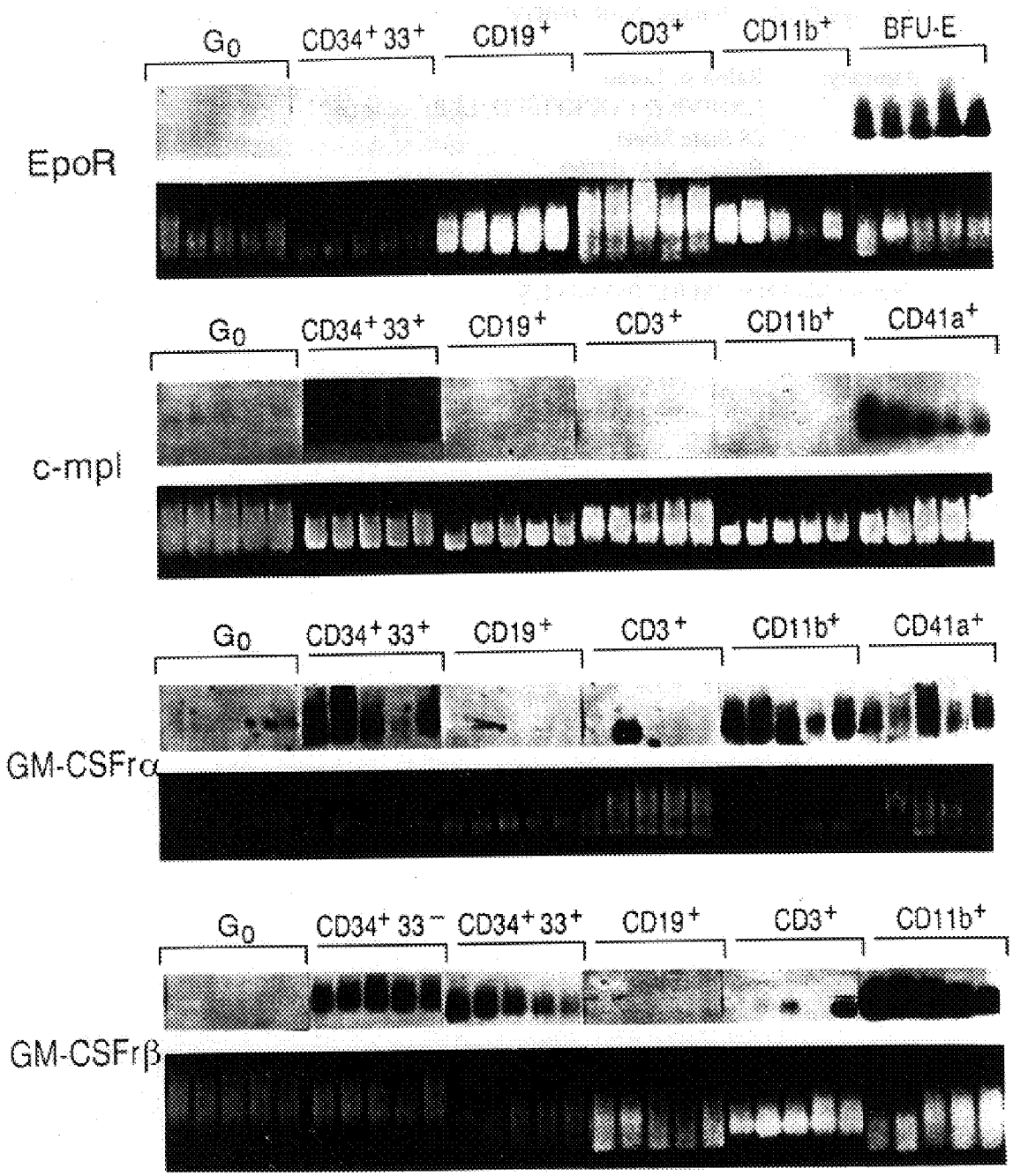
FIG. 4A and 4B depicts the results of experiments showing the analysis of cytokine receptor gene expression in single cells representing various stages of hematopoietic differentiation. The lower panel of each receptor set is the ethidium bromide stained cellular DNA subsequently transferred to a nylon filter, probed with the indicated receptor CDNA and autoradiographed (upper panel).
Figure 4B:
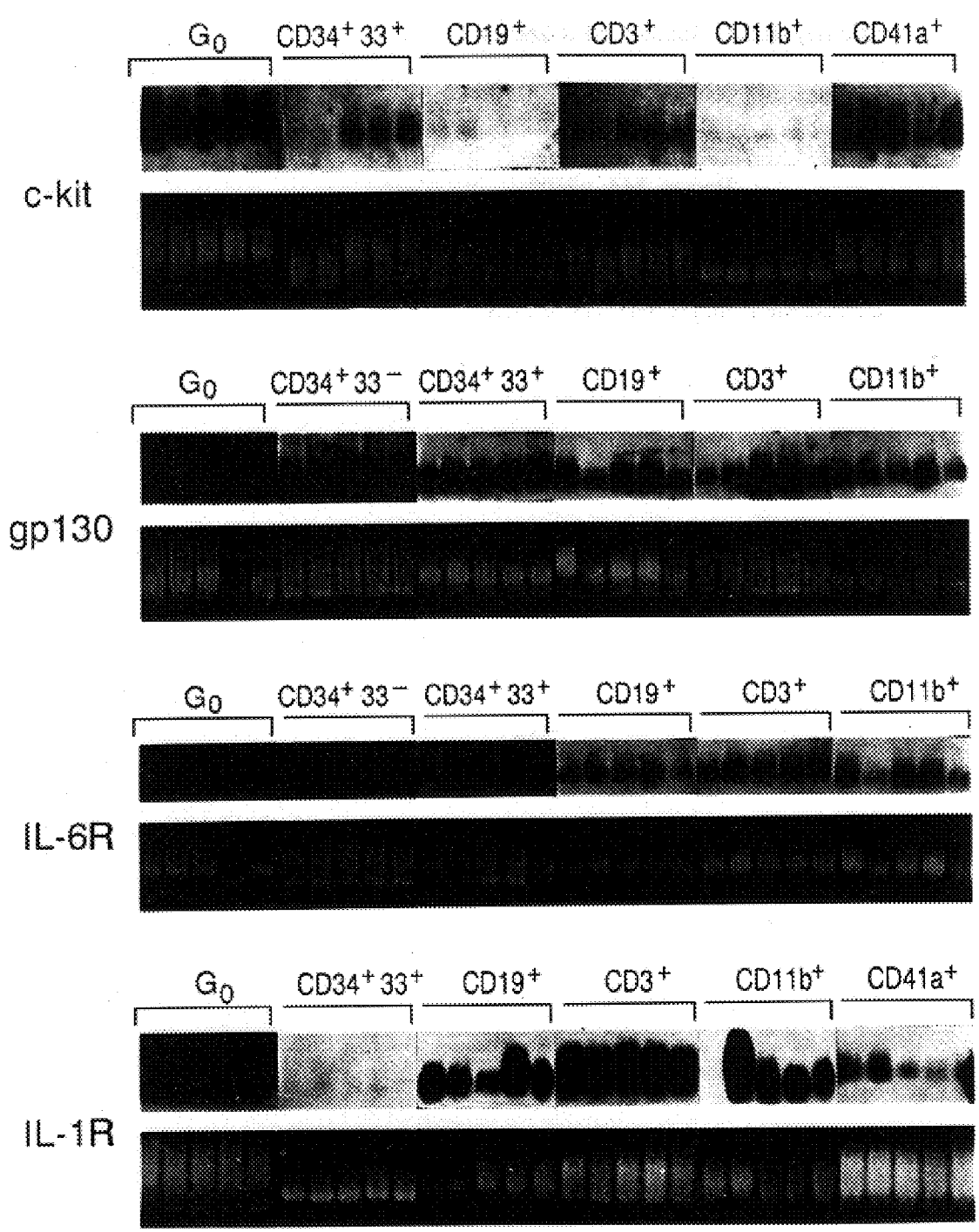

To further evaluate the characteristics of the selected cells, individual cells were isolated in microliter wells, RNA prepared and cDNA generated as described in Example 6. This polymerase chain reaction based, non-specific amplification of cDNA was performed on multiple, single cell representatives of populations of bone marrow and blood cells at various stages of differentiation. Panels of cDNAs were then probed for the presence of message of cytokine receptors. To confirm that the panels of cDNAs represented differentiation specific subsets of cell, clones from receptors whose expression is known to be cell type specific were initially probed (FIG. 4A and 4B) as described in Example 6. The erythropoietin receptor was selectively present in cDNA derived from the dispersed cells of an early burst-forming unit-erythroid (BFU-E) as would be predicted from functional and protein binding studies (H. Youssoufian, et al., *Blood* 81:2223 (1993); P. Sistonen, et al., *Human Genetics* 92:299 (1993); A. Wickrema, et al., *Blood* 80:1940 (1992)). Similarly, the transcript for c-mpl (R. C. Skoda et al., *EMBO J.* 12:2645 (1993); I. Vigon et al., *Proc. Natl. Acad. Sci. U.S.A.,* 89:242 (1992)), associated with megakaryocytic differentiation, was detected in CD41 a selected cells (megakaryocytes) and CD34+/CD33+ cells from which megakaryocytes descend. Unexpectedly, the subselected stem cells also expressed c-mpl. The GM-CSF alpha receptor was expressed on mature CD11 b+ (granulocytic and monocytic) and CD41a+ (megakaryocytic) cells as well as the common precursor to these cells, CD34+/CD33+, an observation consistent with the known responsiveness of these cell types to GM-CSF. (U. Testa et al., *Blood* 81:1442 (1993); S. Chipa et al., *Cell Regulation* 1:327 (1990); Y. Nakagua, et al., GenBank, Accession number D26616, (1994); K. Hayashida et al., *Proc. Natl. Acad. Sci. U.S.A.* 87:9655 (1990); K. Yamasaki et al., *Science* 241:825 (1988); J. E. Sims et al., *Proc. Natl. Acad. Sci. U.S.A.* 86:8946 (1989); F. H. Qiu et al., *EMBO J.* 7:1003 (1988)).

When receptors that have been functionally demonstrated to be present on a wide range of hematopoietic cells were used as probes, very different patterns of expression were noted. The gp130 subunit shared by multiple cytokine receptors such as IL-6, IL-11, leukemia inhibitory factor (LIF), oncostatin M and ciliary neurotrophic factor (CNTF) appeared to be present in all cell types tested. Responsiveness to IL-1 and IL-6 has been noted for multiple hematopoietic cell types including primitive cells (N. Sato et al., *Blood* 82:3600 (1993); M. O. Muench, et al., *Exp. Hematol.* 20:339 (1992); J. L. Escary, et al., *Nature* 363:361 (1993); D. P. Gearing et al., *Science* 255:1434 (1992); M. Hibi et al., *Cell* 63:1149 (1990)) and cDNA for both was detectable in most cells tested including stem cells. The lack of detectable message in CD34+, CD33+ was consistent and unexpected.

To further confirm that the population of cells subselected using KL and IL-3 was not responsive to these cytokines, the cDNA was probed for the respective receptors. As the immunophenotype data had predicted, c-kit message was detected. However, no message for the beta chain shared between the GM-CSF and IL-3 receptors was detected thus accounting for the lack of response to IL-3. Since KL induces proliferative responses only in the presence of a second cytokine and may act alone as a survival factor (N. Katayama, et al., *Blood* 81:610 (1993)), these data are consistent with the functional isolation strategy employed.

The studies reported here exploit observed functional characteristics as cells proceed along hematologic differentiation programs to isolate subsets of primitive cells. The subfraction of human bone marrow cells isolated using this strategy were highly enriched for quiescent, long term culture-initiating cells (LTC-IC) (73% +/−95% C.I. 8%) with a CD34+, CD38−, CD33−, HLA-DR−, CD45Ra−, CD19− and c-kit+ immunophenotype. Single cell cultures were capable of yielding both myeloid and lymphoid progeny. Analysis of individual cells indicated that this primitive subset of cells expressed mRNA for c-kit, gp130, c-mpl and the interleukin-1 and interleukin-6 receptors, but not for the alpha subunit of the GM-CSF receptor, the shared beta subunit of the GM-CSF and IL-3 receptors or the erythropoietin receptor. This simple functional strategy of cell isolation led to the purification of cells with characteristics of hematopoietic stem cells. The degree of enrichment was greater than that typically achieved by antigen or flow cytometric methods of stem cell isolation and avoided problems associated with those methods.

The method described herein is useful for efficiently obtaining human stem cells and can be adapted to the scale necessary for clinical applications. The present method avoids the mechanical trauma of multiple rounds of cell sorting and the potential perturbation of cell function induced by antibody binding. Further, this strategy is potentially applicable to clinical situations since the mechanical handling of the cells is minimal. The output of this isolation strategy is a highly enriched subfraction of multipotent cells with in vitro characteristics consistent with repopulating stem cells. If stem cell gene transduction is desired, this method can augment the specific targeting of such cells, particularly important when virus based transduction strategies are involved. Further, the relative purity of this population lends itself to the molecular study of the events regulating the quiescent stem cell as indicated by the cDNA panels presented above.

In particular, the quiescent pluripotent hematopoietic progenitor cells of the present invention are useful in a method of evaluating the hematopoietic activity of a compound. A compound, either naturally occurring or synthetically produced, may be evaluated regarding its activity to stimulate precursor cells to differentiate. The evaluation method can include the following steps of contacting a population of quiescent pluripotent hematopoietic progenitor cells with the compound to be tested and maintaining the culture under conditions sufficient to allow the cells to proliferate, recovering the cells from culture and evaluating the cells for differentiation characteristics. These differentiation characteristics would include, for example, cell surface markers that can be detected by antibodies, staining with specific dyes or receptor expression. The presence of these differentiation characteristics would be indicative of the hematopoietic activity of the compound.

The cell population obtained by the present invention is also useful in therapeutic methods and clinical applications such as stem cell transplantation. The quiescent pluripotent hematopoietic progenitor cells have been described herein as having the capability of differentiation into cells capable of forming both myeloid and lymphoid cells, as found in normal bone marrow. Thus, the cell population of the present invention has the capability of repopulating mammalian bone marrow. Such a population of cells can be introduced into an individual, who, for example, is affected by a disease that is characterized by abnormal hematopoietic cell production, such as a leukemia. The individual may, or may not be treated in a manner such that the individual's endogenous bone marrow is rendered incapable of producing hematopoietic cells. Such treatment is well known to those of skill in the art and can include radiation or chemotherapy treatment.

Once introduced into the individual, the quiescent pluripotent hematopoietic progenitor cells are stimulated to reconstitute the individual's bone marrow with myeloid and lymphoid cells.

This invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLE 1

Selection of Quiescent Pluripotent Hematopoietic Progenitor Cells

Heparinized bone marrow was obtained from normal volunteers who provided written informed consent to a New England Deaconess Hospital Institution Reviewed Board approved protocol. The cells were layered on Ficoll-Paque (1.077 g/cm$^3$; Pharmacia, Piscataway, N.J., U.S.A.), and centrifuged (850×g, 22° C., 20 min. The low density mononuclear cells were collected from the interface, washed twice with PBS, resuspended in Iscove's modified Dulbecco's medium (IMDM; Gibco, Grand Island, N.Y., U.S.A.) containing 15% fetal calf serum (FCS; HyClone, Logan, Utah, U.S.A.) and plated in 75 cm$^2$ flasks (1–2×10$^7$ cells in 10 ml). After an overnight incubation at 37° C. in a humidified 5% CO$_2$ cell culture incubator, the non-adherent cells were recovered.

For some experiments, the non-adherent cells were then incubated with an anti-CD34 monoclonal antibody (Amac, Wesbrook, Me., U.S.A.) at 4° C. for 30 min, washed and mixed with magnetic microspheres coated with anti-mouse-IgG (Dynal Inc.; Great Neck, U.S.A.) at a 0.5–1 bead per cell ratio. Rosetted cells were recovered permanent magnet and then washed 3 times with IMDM.

Unfractionated or $CD34^+$ enriched bone marrow mononuclear cells ($2\times10^5$ cells/ml) were incubated at 37° C., 5% $CO_2$ for seven days with 0.6 mg/ml 5-fluorouracil (5-FU; Solo Pack, Elk Grove Village, Ill., U.S.A.) in IMDM medium supplemented with 10% FCS, Kit ligand-Stem Cell Factor (SCF 100 ng/ml; Amgen, Thousand Oaks, Calif.) and interleukin-3 (IL-3 100 ng/ml; Genzyme, Cambridge, Mass., U.S.A.). The cell population that survived 5-FU treatment was used in this study.

Cells were stained with propidium iodide (PI) and Hoechst 33342 (HO) as previously described (A. Pollack, G. Ciancio, METHODS IN CELL BIOLOGY, Z. Darzynkiewicz, H. A. Crissman Eds. (Academic Press, Inc. 1990) vol. 33. Cells were washed in PBS, resuspended in 100 ul PBS containing 20 $\mu$g/ml propidium iodide (PI) and 10 ug/ml RNase and incubated for 30 min. on ice. Thereafter 1.9 ml of 25% ethanol and 10 $\mu$l 1 mM HO-33342 (HO; Sigma, St. Louis, Mo., U.S.A.) was added and the cells were incubated for another 30 min. on ice. HO and PI fluorescence were analyzed using an EPICS 750 series flow cytometer (Coulter Electronics, Hialeah, Fla.). Fluorescence was excited by a 5 watt argon ion laser generating 40 mW of light at 351–363 nm. HO emission was detected through a 450 nm band pass filter. PI emission was detected through a 610 nm long pass filter. Fluorescence from each dye was directed to the appropriate detectors using a 560 nm short pass dichroic filter. Scattered laser light was eliminated from the fluorescence detectors by a 380 nm long pass filter.) followed by flow cytometric analysis on days 0 and 7.

HO staining intensity varies with DNA content and increases as cells transit from $G_0$–$G_1$ into S and $G_2$-M phase of the cell. PI staining increases with either loss of viability ($PI_{mod,hi}$, $HO_{lo}$) or as cells undergo $S_1$ G2 and M phase ($PI_{mod,hi}$, $HO_{mod,hi}$). Under control conditions the full spectrum of the cell cycle was represented as indicated by variable HO staining with a proportion of non-viable cells ($PI_{mod,hi}$, $HO_{lo}$) increasing during the 7 incubation period as would be expected from terminally differentiated myeloid cells in liquid culture. However, the 5-FU treated cells are restricted to $HO_{lo}$ staining and had an increased proportion of non-viable cells. A remaining small subpopulation of viable cells ($PI_{lo}$, $HO_{lo}$) in the 5-FU treated cultures was confirmed by trypan blue exclusion analysis. Similar results were obtained using either CD34+ selected (lower panel) or bulk preparations of bone marrow mononuclear cells (upper panel) as shown in FIG. 1.

EXAMPLE 2

Evaluation of Cell Proliferation

Bone marrow mononuclear cell proliferation was evaluated by staining with the stable membrane dye, PKH26 (Zynaxis, Malvern, Pa.), and evaluated by flow cytometry (FACScan, Becton-Dickenson, San Jose, Calif.) using the FL2 channel. PKH26 stains cells differentially based on the cell type, thought to be the basis for the range of overlapping peaks when using unselected bone marrow mononuclear cells (upper panel). As cells undergo division, PKH26 partitions in the progeny and thus is diluted out at each cell division. Under control conditions the PKH26 fluorescence intensity initially shifts and narrows (day 4) as cells proliferate or die and then broadens as the remaining myeloid progenitors proliferate (day 7). In contrast, the 5-FU treated cells maintain high signal intensity indicating that the selection strategy spares cells not undergoing cell division.

EXAMPLE 3

Morphological Studies

Control cells (magnification 400×) were large with active mitosis evident while 5-FU selected cells (magnification 1000×) were uniformly small with dense nuclei and only a faint rim of cytoplasm. As shown in FIG. 3, following single cell long term bone marrow culture, progeny were variable in size with some clusters of large cells (C) (magnification 400×) staining positively for monocyte specific alpha-naphthyl esterase (D); dispersed cells and some clustered larger cells were negative for alpha-naphthyl esterase. Smaller, dispersed cells (magnification 1000×) stained positively for the B-cell specific CD19 (D); clustered, large cells were negative for CD19.

EXAMPLE 4

Methoxycellulose Culture Studies

Cells were either cultured in methylcellulose cultures immediately after selection or following co-cultivation with an irradiated, adherent human bone marrow stromal cell layer. Stromal cell cultures were established and maintained according to a modified method (L. Columbel, et al., *Blood* 62:291 (1983); C. Eaves, et al., *J. Tiss. Cult. Meth.* 13:55 (1991); $10^7$ bone marrow mononuclear cells were suspended in a T25 flask in 5 ml of long term culture (LTC) medium: IMDM with 12.5% FCS, 12.5% horse serum (HS; Gibco, Grand Island, N.Y., U.S.A.), 1,000 U/mL penicillin, 100 U/mL streptomycin, $5\times10_{-6}$ mol/L $\alpha$-thioglycerol, and $10^{-6}$ mol/L hydrocortisone (Sigma, St Louis, Mo., U.S.A.) and cultured 4–5 days 37° C. in a humidified atmosphere with 5% $CO_2$. The culture was then transferred to 33° C. and grown until confluent at which time the cells were trypsinized, washed, irradiated (15 Gy) and subcultured in 96-well flatbottomed Nunclon microwell plates at a density of $3\times10^4$ cells/cm$^2$. After 1–5 days, selected or control non-adherent bone marrow mononuclear cells were seeded at 0, 1, 5, 10 or 100 cells per well with 24 replicate wells per cell concentration. After 5 weeks, the wells were trypsinized, washed and plated in standard methylcellulose assays which were scored qualitatitively at 14 and 21 days for colony formation.) This assay depends upon the cultivation of non-adherent cells with a stromal feeder layer for five weeks before assaying for a more differentiated phenotype, the ability of cells to generate colonies in a semi-solid matrix (a methylcellulose colony assay). Colonies of mixed erythroid, granulocyte and monocyte/macrophage cells (CFU-mix) were scored two weeks following plating in methylcellulose. The number of $G_0$ cells initially plated on the subconfluent stromal feeder layers in 24 well plates is indicated; these cultures were demi-depopulated weekly and the non-adherent cells plated in the methylcellulose cultures.

EXAMPLE 5

Limiting Dilution Long-Term Cultivation Initially Cell Assay

Limiting dilutions long term culture-initiating cell (LTC-IC) assay results from the wells plated at 1 cell/well in 24 replicates in 5 independent experiments. Wells yielding colonies in methylcellulose were scored as positive. Data from all wells are shown in the right two columns; data normalized to the maximum number of wells positive with either the 5, 10 or 100 cells/well samples are shown in the left 2 columns. No colonies were seen in any control (0 cells/well) wells; no statistically significant differences between the 5, 10 or 100 cells/well samples were detected. Control CD34 + bone marrow mononuclear cells similarly plated yielded an estimated LTC-IC frequency of 3.3–5.0% when evaluated by Poisson 35 analysis (C. Taswell, *J. Immunol.* 126:1614 (1981); E. Porter, R. J. Berry, *Br. J. Cancer* 17:583 (1963)).

EXAMPLE 6

Molecular Characteristics of Selected Cells

Panels of 5 cells of each type were used to avoid individual cell artifacts; individual cell differences may represent heterogeneity in the cell subset or contamination by extraneous cells. The amplification schema results in variable length cDNAs from any given transcript, resulting in smears rather than bands when hybridized to a corresponding probe. Single cells were plated in a 96-well plate using a Becton-Dickenson cell dispersion unit instrument directly into 4 μl lysis buffer (50 mM Tris-HCl pH-8.3, 75 mM KCl, 3 mM $MgCl_2$, 2 μM of each deoxyribonucleotide triphosphate (Pharmacia), 100 ng/ml (dT)24, 100 U/ml Inhibit Ace (5'-3' Inc.), 2000 U/ml RNAguard (Pharmacia) and 0.5% NP-40). The samples were heated to 65° C. for 1 min, cooled to 22° C. for 3 min and put on ice. The resultant lysate was then subjected to reverse transcription and polymerase chain reaction as previously described. (G. Brady, et al., *Mol. Cell. Biol.* 2:17 (1990); L. H. Trumper et al., *Blood* 81:3097 (1993); One hundred units of Moloney (Gibco-BRL) and 2 units avian reverse transcriptase (Promega, Madison, Wis., U.S.A.) were added and the samples were incubated at 37° C. for 15 min. The reverse transcriptases were thereafter inactivated at 65° C. for 10 min. Cell free and reverse transcriptase free samples were used as negative controls. Poly(A) tailing of the single cell cDNA was done in 200 mM potassium cacodylate, 4 mM $CoCl_2$, 0.4 mM DTT, 10 units of terminal transferase (Boehringer Mannheim, Indianapolis, Ind., U.S.A.). After the addition of 200 μM dATP the samples were incubated at 37° C. for 30 min. After heat inactivation of the enzyme the cDNA was either amplified immediately or stored at −80° C. until use. 20 μl of the tailed cDNA was added to 30/μl of PCR buffer containing 10 mM Tris-HCl pH=8.3, 50 mM KCl, 2.5 mM $MgCl_2$, 1 mM dNTP 0.05% Triton X-100, 5 μM $(dT)_{24}X$ primer and 5 units of Taq polymerase (Perkin-Elmer Cetus, Newton Centre, Mass., U.S.A.). The sequence of the PCR primer $(dT)_{24}X$ primer was ATG TCG TCC AGG CCG CTC TGG ACA AAA TAT GAA TTC dT (SEQ ID NO: 1) (C. Taswell, *J. Immunol.* 126: 1614 (1981); E. Porter, R. J. Berry, *Br. J. Cancer* 17:583 (1963)). Amplification was done for 25 cycles (1 min. at 94° C., 2 min. at 42° C. and 6 min. at 72° C. plus 10 seconds extension/cycle). Thereafter an additional 5 units of Taq polymerase was added, followed by another 25 cycles of amplification. cDNA probes were labelled with $^{32}$P-dCTP (DuPont NEN Research Products, Boston, Mass., U.S.A.) using random primed DNA labelling (Stratagene, La Jolla, Calif., U.S.A.). Oligonucleotide probes were end labelled using $^{32}$P-ATP (DuPont NEN Research Products) using $T_4$ polynucleotide kinase (DuPont NEN Research Products). Southern blots were prepared by running 20 μl aliquots of the amplified cDNA on 1% agarose gels followed by transfer to nylon membranes (Micron Separation Inc, Westboro, Mass., U.S.A.). The membranes were prehybridized in prehybridization buffer (50% formamide, 6xSSPE, 5x Denhardt's solution, 0.5% SDS, 50 μg/ml denaturated ssDNA for cDNA probes or 20% formamide, 6xSSPE, 2xDenhardt's solution and 100 μg/ml ssDNA for oligonucleotide probes) at 42° C. for 3–6 hours. Hybridization was carried out for 16–18 hours at 42° C. in hybridization solution (50% formamide, 5X Denhardts, 6xSSPE, 0.2% SDS, 100 μg/ml denatured ssDNA, and $2\times10^6$ cpm)ml radioactively labeled probe oligonucleotide). The membranes were washed with medium stringency (1x5 min with 5xSSC, 0.5% SDS at room temperature, 2x15 min with 1xSSC 0.5% SDS at 37° C., 2x min with 0.2xSSc, 0.5% SDS at 40° C) and exposed to X-ray film at −80° C. for 4 hours to 1 week.)

Following electrophoresis and transfer to a nylon membrane, the resultant blots were hybridized with $^{32}$P-radiolabelled probes from cytokine receptor cDNAs including extreme 3' sequences. cDNA clones of the human erythropoietin (EPO) receptor (kindly provided by Dr. Mark Showers, Brigham and Women's Hospital, Boston, Mass.) (15). Human granulocyte-macrophagecolony-stimulating factor (GM-CSF) receptor alpha and beta chains (U. Testa et al., *Blood* 81:1442 (1993); S. Chipa et al., *Cell Regulation* 1:327 (1990); Y. Nakagua, et al., GenBank, Accession number D26616, (1994); K. Hayashida et al., *Proc. Natl. Acad. Sci. U.S.A.* 87:9655 (1990); K. Yamasaki et al., *Science* 241:825 (1988); J. E. Sims et al., *Proc. Natl. Acad. Sci. U.S.A.* 86:8946 (1989); F. H. Qiu et al., *EMBO J.* 7:1003 (1988)) and human c-kit (kindly provided by Dr. Tim Ernst, Dana-Farber Cancer Institute, Boston, Mass.) were used as probes. Oligonucleotide probes from the cDNA sequence of human c-mpl (CAGATCAGCTGGGAGGAGCCAAGCA-CTGAACTTCACCGTCGC) (SEQ ID NO: 2) (R. C. Skoda et al., *EMBO J.* 12:2645 (1993); I. Vigon et al., *Proc. Natl. Acad. Sci. U.S.A.,* 89:242 (1992)), the human interleukin-1 (IL-1) receptor (U. Testa et al., *Blood* 81:1442 (1993); S. Chipa et al., *Cell Regulation* 1:327 (1990); Y. Nakagua, et al., GenBank, Accession number D26616, (1994); K. Hayashida et al., *Proc. Natl. Acad. Sci. U.S.A.* 87:9655 (1990); K. Yamasaki et al., *Science* 241:825 (1988); J. E. Sims et al., *Proc. Natl. Acad. Sci. U.S.A.* 86:8946 (1989); F. H. Qiu et al., *EMBO J.* 7:1003 (1988)). (ATAGCAGCCCAGGGCACTTCAGAGTAAGAGGGC-TTGGGAAGATCTTTTAAAA) (SEQ ID NO: 3), human interleukin-6 (IL-6) (U. Testa et al., *Blood* 81:1442 (1993); S. Chipa et al., *Cell Regulation* 1:327 (1990); Y. Nakagua, et al., GenBank, Accession number D26616, (1994); K. Hayashida et al., *Proc. Natl. Acad. Sci. U.S.A.* 87:9655 (1990); K. Yamasaki et al., *Science* 241:825 (1988); J. E. Sims et al., *Proc. Natl. Acad. Sci. U.S.A.* 86:8946 (1989); F. H. Qiu et al., *EMBO J.* 7:1003 (1988)) receptor (CTTACTTAGGTGTGGGGGAAGCACCATAACTTGT-TTAGCCCAAAACCAAG) (SEQ ID NO: 4) or human gp 130 (CTGTACGGCAAGGCGGCTACATGCCTCAGTG-AAGGACTAGTAGTT) (SEQ ID NO: 5) (N. Sato et al., *Blood* 82:3600 (1993); M. O. Muench, et al., *Exp. Hematol.* 20:339 (1992); J. L. Escary, et al., *Nature* 363:361 (1993); D. P. Gearing et al., *Science* 255:1434 (1992); M. Hibi et al., *Cell* 63:1149 (1990)) were also radiolabelled and used as probes.

Equivalents

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A method of screening a compound for hematopoietic activity comprising the steps of:
 a) contacting a population of quiescent pluripotent hematopoietic progenitor cells obtained by culturing a mammalian hematopoietic mononuclear cell suspension in the combined presence of at least one anti-metabolite agent and at least one early-acting growth factor under conditions sufficient to eliminate dividing cells and cells responsive to early-acting growth factors with a compound to be tested for hematopoietic activity and maintaining the culture under conditions sufficient for proliferation of the cells; and
 b) recovering the cells of step a) and evaluating the cells for differentiation characteristics whereby the presence of differentiation characteristics are indicative of the hematopoietic activity of the compound.

2. The method of claim 1, wherein the mammalian hematopoietic mononuclear cell suspension is obtained from a human.

3. The method of claim 1, wherein the mammalian hematopoietic mononuclear cell suspension is obtained from a cell source selected from the group consisting of spleen, liver, thymus, bone marrow, umbilical cord blood, and peripheral blood.

4. The method of claim 1, wherein the anti-metabolite agent is selected from the group consisting of 5-fluorouracil and bromodeoxy uridine.

5. The method of claims 1, wherein the early-acting growth factor is selected from the group consisting of kit ligand, stem cell factor, interleukin-3, interleukin-6, interleukin- 1, interleukin-11, flt-3 ligand and mpl ligand.

\* \* \* \* \*